United States Patent [19]
Hillard et al.

[11] 4,322,359

[45] Mar. 30, 1982

[54] PROCESS FOR THE PREPARATION OF 2,5-DIMETHYL-1,4: 3,6-DIANHYDROSORBITOL

[75] Inventors: Ray L. Hillard, Annandale; Irwin D. Greene, Somerset, both of N.J.

[73] Assignee: American Cyanamid Company, Stamford, Conn.

[21] Appl. No.: 245,556

[22] Filed: Mar. 19, 1981

[51] Int. Cl.³ .............................................. C07D 493/04
[52] U.S. Cl. .................................................. 260/347.8
[58] Field of Search ....................................... 260/347.8

[56] References Cited

U.S. PATENT DOCUMENTS 4,169,152 9/1979 Le Maistre et al. .......... 260/347.8 X

OTHER PUBLICATIONS

Montgomery et al., J. Chem. Soc. (1946) pp. 390–393.

*Primary Examiner*—Richard Raymond
*Attorney, Agent, or Firm*—Frank M. Van Riet

[57] ABSTRACT

A water-miscible, non-hydroxylic, organic solvent is employed in the production of 2,5-dimethyl-1,4: 3,6-dianhydrosorbitol by methylation of 1,4: 3,6-dianhydrosorbitol with dimethyl sulfate.

10 Claims, No Drawings

PROCESS FOR THE PREPARATION OF 2,5-DIMETHYL-1,4:3,6-DIANHYDROSORBITOL

BACKGROUND OF THE INVENTION 2,5 Dimethyl-1,4:3,6-dianhydrosorbitol (also known as dimethylisosorbide) exhibits excellent organic solvent characteristics in both water and in other organic solvents, and has many potential uses in pharmaceutical and cosmetic formulations.

In view of important potential pharmaceutical uses for dimethylisosorbide, there is a need for a simple, productive and inexpensive process for its preparation.

Montgomery and Wiggens, *J. Chem. Soc.* 1946, p. 390–393, reported the methylation of isosorbide with dimethyl sulfate and 30% aqueous sodium hydroxide using water as the solvent. The yield of dimethylisosorbide was reported to be 77%.

Water is not a suitable solvent for the commercial methylation of isosorbide with dimethyl sulfate since this reagent is readily hydrolyzed in the presence of base, resulting in significant yield loss and resultant higher economic outlays. Hydroxylic solvents, such as ethanol, are competitive with the isosorbide in the methylation reaction and provide low or no yields of product while organic solvents such as toluene or methylene chloride are not suitable solvents because the alkali metal salts of isosorbide are not soluble therein.

Therefore, the need exists to uncover a useful process for the preparation of dimethylisosorbide in high yields and at the lowest possible cost.

SUMMARY OF THE INVENTION

In accordance with the present invention, it has now been discovered that isosorbide may be readily methylated using dimethyl sulfate at atmospheric pressure and relatively low temperature in the presence of a suitable organic, water-miscible, non-hydroxylic solvent and an alkali metal base. Dimethylisosorbide is recovered in accordance with the process of the present invention in high yield, that is, about 90% or higher.

DESCRIPTION OF THE INVENTION INCLUDING PREFERRED EMBODIMENTS

The present invention comprises a process for the preparation of 2,5-dimethyl-1,4:3,6-dianhydrosorbitol from 1,4:3,6-dianhydrosorbitol by methylation with dimethyl sulfate, wherein a stoichiometric excess of dimethyl sulfate is added to a solution of a dialkali metal salt of 1,4:3,6-dianhydrosorbitol in a water-miscible, non-hydroxylic organic solvent at a temperature of from about 25° C. to the boiling point of the solvent and recovering the resultant product.

More particularly, the present invention comprises a process for the preparation of 2,5-dimethyl-1,4:3,6-dianhyudrosorbitol from 1,4:3,6-dianhydrosorbitol wherein a stoichiometric excess of dimethyl sulfate is added to a solution of 1,4:3,6-dianhydrosorbitol in a water-miscible, non-hydroxylic organic solvent at a temperature of from about 25° C. to the boiling point of the solvent; the solvent is removed from the reaction mixture, the resultant aqueous solution of crude 2,5-dimethyl-1,4:3,6-dianhydrosorbitol is extracted; the methylene chloride is removed from the extracted solution thereof, and the product is purified.

Thus, in accordance with the present invention, isosorbide is methylated with dimethyl sulfate at atmospheric pressure in the presence of an alkali metal base and a water-miscible, non-hydroxylic organic solvent.

A suitable solvent is one in which isosorbide, its alkali metal salts, and dimethylisosorbide are soluble under the conditions of the reaction. The preferred solvent is acetone. Additional useful solvents include the ketones such as methylethylketone; dimethylformamide; tetrahydrofuran; dioxane; glyme; diglyme and the like.

The methylation is conducted using a slight excess of dimethyl sulfate over the stoichiometrically required amount. An excess of about 5 mole percent is preferred.

The use of an alkali metal base is necessary in order to bring the isosorbide solution to an alkaline condition before and during the methylation procedure. Suitable alkali metal bases include alkali metal hydroxides, alkali metal bicarbonates, and alkali metal carbonates. Suitable alkali metal compounds include those of sodium, potassium, lithium and the like. Since 2 moles of water are produced in the methylation reaction, it is desirable to minimize the amount of additional water added to the reaction mixture. A preferred alkali metal base is concentrated aqueous solution of sodium hydroxide, for example, a 50% aqueous sodium hydroxide solution. Alkali metal bicarbonates and carbonates may also be used since the rate of hydrolysis of dimethyl sulfate may be reduced thereby.

As a rule, the amount of alkali metal base used in the reaction will be slightly in excess of that required stoichiometrically. In practice, about a 10 mole percent excess is used in order to destroy any unreacted dimethyl sulfate remaining on completion of the methylation reaction.

It is necessary for the isosorbide solution to be rendered alkaline before methylation commences. This is accomplished by adding all of the alkali metal base to the solution initially, followed by addition of the dimethyl sulfate, or by adding a small amount of alkali metal base initially, followed by the simultaneous addition of alkali metal base and dimethyl sulfate in a manner such that there is no significant excess of dimethyl sulfate in the reaction mixture at any time during the reaction.

The methylation reaction is exothermic, and oftimes requires external cooling. It is preferred to add the dimethyl sulfate at a rate which will sustain the reaction at or near the refluxing temperature, for example, about 55°–60° C. using acetone. The reaction is generally completed upon the completion of the dimethyl sulfate addition. Additional heating beyond this point may be effected to insure that any unreacted dimethyl sulfate is destroyed by alkaline hydrolysis.

When the reaction is completed, the solvent is removed from the reaction mixture such as by stripping etc. and the resulting aqueous solution of dimethylisosorbide and alkali metal salts is extracted such as with a suitable solvent to remove the dimethylisosorbide therefrom. A generally useful solvent for this purpose is methylene chloride. Any color bodies may then be removed by washing the organic solvent solution with aqueous sodium hydroxide.

The organic solvent solution is then freed of solvent such as by stripping and residual dimethylisosorbide is purified such as by vacuum distillation. The yield of product obtained by the process of the invention is 90% or higher.

Both the reaction solvent, for example, acetone, and the extractant, for example, methylene chloride, are preferably recovered and recycled for reuse in the process.

The following examples are set forth for purposes of illustration only and are not to be construed as limitations on the present invention except as set forth in the appended claims. All parts and percentages are by weight unless otherwise specified.

EXAMPLE 1

A solution of 500 parts of isosorbide in 1090 parts of acetone is charged to a stirred reaction vessel. Dimethyl sulfate (907.3 parts) and 50% aqueous sodium hydroxide solution (603 parts) are separately, but simultaneously, added portionwise to the stirred solution of isosorbide over a period of about 2 hours. The rate of addition of sodium hydroxide is slightly faster than that for dimethyl sulfate. The heat of reaction is sufficient to sustain the reaction mixture at a temperature approximating the refluxing temperature. When the addition is complete, the acetone is distilled from the reaction mixture. Water (400 parts) is added after 300 parts of acetone are removed and the distillation is continued until the distillation head temperature reaches 97° C. An additional 480 parts of water are then added to the residue and the aqueous solution is extracted twice with a total of 1320 parts of methylene chloride. The extracts are combined and a portion thereof is analyzed by gas chromatography for dimethyl isosorbide; yield is 90.2%.

A portion (380 parts) of the methylene chloride solution is extracted twice with 200 part portions of 5 N sodium hydroxide solution. A portion (185 parts) of the base extracted solution is concentrated to remove methylene chloride and the residue is vacuum distilled to yield 42.2 parts of dimethyl isosorbide (82.6% yield), bp 125°–129° C. (20 mm Hg).

EXAMPLE 2

The procedure of Example 1 is again followed except that the sodium hydroxide solution is replaced by an equivalent amount of a 45% aqueous potassium hydroxide solution. Similar results are achieved.

EXAMPLE 3

Again following the procedure of Example 1 except that the acetone is replaced by dioxane, similar results are achieved.

EXAMPLES 4–7

Using (4) dimethylformamide, (5) glyme, (6) tetrahydrofuran and (7) methylethylketone as replacements for acetone under the procedure of Example 1, results in the recovery of dimethyl isosorbide in substantially equivalent yields.

We claim:

1. A process for the preparation of 2,5-dimethyl-1,4:3,6-dianhydrosorbitol from 1,4:3,6-dianhydrosorbitol by methylation with dimethyl sulfate, which comprises adding a stoichiometric excess of dimethyl sulfate to a solution of an alkali metal base and 1,4:3,6-dianhydrosorbitol in a water-miscible, non-hydroxylic organic solvent at a temperature of from about 25° C. to the boiling point of the solvent and recovering the resultant 2,5-dimethyl 1,4:3,6-dianhydrosorbitol.

2. A process in accordance with claim 1 wherein the solvent is acetone.

3. A process in accordance with claim 1 wherein the alkali metal base is sodium hyroxide.

4. A process in accordance with claim 1 wherein the alkali metal base is potassium hydroxide.

5. A process for the preparation of 2,5-dimethyl-1,4:3,6-dianhydrosorbitol from 1,4:3,6-dianhydrosorbitol which comprises adding a stoichiometric excess of dimethyl sulfate to a solution of 1,4:3,6-dianhydrosorbitol and an alkali metal base in a water-miscible, non-hydroxylic organic solvent at a temperature of from about 25° C. to the boiling point of the solvent; removing the solvent from the reaction mixture; extracting the aqueous solution of crude 2,5-dimethyl-1,4:3,6-dianhydrosorbitol; removing the methylene chloride from the extracted solution thereof, and purifying the product.

6. A process in accordance with claim 5 wherein the solvent is recovered and recycled for use in the methylation reaction.

7. A process in accordance with claim 5 wherein the extraction is effected with methylene chloride and the organic solvent is acetone.

8. A process in accordance with claim 7 wherein the methylene chloride is recovered and recycled for use in the extraction step.

9. A process in accordance with claim 5 wherein the solvent is removed by distillation.

10. A process in accordance with claim 5 wherein the product is purified by vacuum distillation.

* * * * *